United States Patent [19]

Reyes

[11] Patent Number: 5,066,579
[45] Date of Patent: Nov. 19, 1991

[54] HTLV-I PEPTIDE ANTIGEN AND ASSAY

[75] Inventor: Gregory R. Reyes, Palo Alto, Calif.

[73] Assignee: Genelabs Incorporated, Redwood City, Calif.

[21] Appl. No.: 366,313

[22] Filed: Jun. 13, 1989

Related U.S. Application Data

[63] Continuation of Ser. No. 948,270, Dec. 31, 1986, abandoned.

[51] Int. Cl.⁵ ............................................ G01N 33/569
[52] U.S. Cl. ......................................... 435/5; 435/7.1; 435/69.3; 435/69.7; 435/69.8; 435/70.1; 435/70.21; 435/240.27; 435/810; 436/548; 436/811; 530/324; 530/387; 530/395; 530/810; 530/828
[58] Field of Search ...................... 435/5, 7, 69.3, 69.7, 435/69.8, 70.1, 70.21, 240.27, 810, 7.1; 436/548, 811; 530/324, 387, 810, 828, 395

[56] References Cited

U.S. PATENT DOCUMENTS

| 4,525,300 | 6/1985 | Yoshida et al. | 260/112.5 R |
|---|---|---|---|
| 4,572,800 | 2/1986 | Shimizu et al. | 260/112.5 R |
| 4,689,398 | 8/1987 | Wu et al. | 530/327 |
| 4,722,888 | 2/1988 | Broder et al. | 530/387 |

OTHER PUBLICATIONS

Schupbach et al., "Antigens on HTLV-IInfected Cells Recognized by Leukemia and Aids Sera Are Related to HTLV Viral Glycoprotein", Science, 224 (1984): 607-610.

Samuel et al., "Diagnostic Potential for Human Malignancies of Bacterially Produced HTLV-I Envelope Protein", Science, 226(1984):1094-1097.

Lee et al., "Human T-Cell Leukemia Virus-Associated Membrane Antigens: Identity of the Major Antigens recognized after Virus Infection", Proceedings of the National Academy of Sciences USA, 81(1984):3856-3860.

Newman et al., "Serological Characterization of Human T-Cell Leukemia (Lymphotropic) Virus, Type I (HTLV-I) Small Envelope Protein", Virology, 150 (1986): 106-116.

Robert-Guroff et al., "A Monoclonal Antibody Specific for a 52,000-Molecular-Weight Human T-Cell Leukemia Virus-Associated Glycoprotein Expressed by Infected Cells", Journal of Virology, 53 (1985):214-220.

Yoshida et al., "Isolation and Characterization of Retrovirus from Cell Lines of Human Adult T-Cell Leukemia and its Implication in the Disease", Proceedings of the National Academy of Sciences USA, 79(1982):2031-2035.

Itamura et al., "Expression of the Gag Gene of Human T-Cell Leukemia Virus Type I in *Escherichia coli* and its diagnostic use", Gene, 38 (1985):57-64.

Tanaka et al., "A Glycoprotein Antigen Detected With New Monoclonal Antibodies on the Surface of Human Lymphocutes Infected With Human I-Cell Leukemia Virus Type-I (HTVL-I)", International Journal of Cancer, 36(1985):549-555.

Seiki et al., "Human Adult T-Cell Leukemia Virus: Complete Nucleotide Sequence of the Proviral Genome Integrated in Leukemia Cell DNA", Proceedings of the National Academy of Sciences USA, 80 (1983):3618-3622.

(List continued on next page.)

*Primary Examiner*—Christine Nucker
*Attorney, Agent, or Firm*—Peter J. Dehlinger

[57] ABSTRACT

A recombinant peptide antigen is provided which is derived from HTLV-I envelope protein gp46 and immunoreactive with anti-HTLV-I antibody present in a individuals with HTLV-I related T-cell leukemia. The antigen is useful as a diagnostic tool in determining whether an individual has been or is infected with HTLV-I, and is also useful in a method of immunizing individuals against such infection.

6 Claims, 2 Drawing Sheets

OTHER PUBLICATIONS

Hattori et al., "Identification of Gag and Env Gene Products of Human T-Cell Leukemia Virus (HTLV)", Virology, 136(1984):338–347.

Kiyokawa et al., "Envelope Proteins of Human T-Cell Leukemia Virus: Expression in *Escherichia coli* and its Application to Studies of Env Gene Functions", Proceedings of the National Academy of Sciences USA, 81(1984):6202–6206.

Huynh et al., in *DNA Cloning, vol.* 1 (ed. D. M. Glover, Washington, D.C.:IRL Press, 1985), pp. 49–78.

Matsushita et al., (1986) Proc Natl Acad Sci (USA) 83:2672–2676.

Miyoshi et al., (1981) Nature 294:770–771.

Poiesz et al., (1980) Proc Natl Acad Sci (USA) 7.7:7415–7419.

Popovic et al., (1983) Science 219:856–859.

```
ThrGlyAlaValSerSerProTyrTrpLysPheThrGlnHisAspValAlaAsnPheThrGlnHisAspValAlaAsnPheThrGlnGluValSerArgLeuAsnIle
TACAGGAGCCGTCCAGCCCCTACTGGAAGTTCAGCACGATGTCAATTTTACTCAAGAAGTTCACGCCCTCAATATT
    ↑
β-GAL ↑ 5565

AsnLeuHisPheSerLysCysGlyPheProSerLeuLeuValAspAlaAlaProGlyTyrAspProIleTrp
AATCTCCATTTTTCGAAATGCGGTTTTCCCTTCTAGTCGACGCTCCAGGATATGACCCCATCTG    5700
                        ↑
                      5664

PheLeuAsnThrGluProSerGlnLeuProProThrAlaProProLeuLeuProHisSerAsnLeuAspHisIleLeu
GTTCCTTAATACCGAACCCAGCCAACTGCCTCCCACCGCCCCTCCACTCCTAACCTAGACCACATCCCTC

GluProSerIleProTrpLysSerLysLeuThrLeuValGlnLeuThrLeuGlnSerThrAsnTyrThr    5850
GAGCCCTCTATACCATGGAAATCAAAACTCCCTGACCCTTGTCCAGTTAACCCTACAAAGCACTAATTATACT
        ↑
      5790    ↑
            5807

CysIleValCysIleAspArgAlaSerThrLeuSerTyrSerProAsnValSerValProSerSer
TGCATTGTGTCTGTATCGATCGTGCCAGCACTCTATACTCTCCCAACGTCTCTGTTCCATCCTCT
                                            ↑
                                        → β-GAL
                                        5895

SerSerThrProLeuLeuTyrProLeuAlaLeuProHisLeuThrLeuProPheAsnTrpThr
TCTTCTACCCCTCCTTACCCTATCCAGCGCTTCCAGCCCCCACCTGACGTTACCATTTAACTGGAC
```

Fig. 1C

HTLV-I PEPTIDE ANTIGEN AND ASSAY

This application is a continuation, of application No. 06,948,270, filed 2/31/86 abandoned.

1. FIELD OF THE INVENTION

The present invention relates generally to human T-cell leukemia virus type I (HTLV-I), and more particularly, to a recombinant peptide antigen which is immunoreactive with anti-HTLV-I-antibody present in individuals infected with HTLV-I, and to assay methods which use the antigen.

2. REFERENCES

Huynh, T.V., et al., in "DNA Cloning, Volume 1, "ed. D.M. Glover, Washington D.C.: IRL Press, 1985 (Chapter 2).

Maniatis, T., et al, *Molecular Cloning: A Laboratory Manual*, Cold Spring Harbor Laboratory (1982).

Matsushita, S., et al., *Proc Natl Acad Sci* (USA), 83:2672 (1986).

Miyoshi, I., et al, *Nature*, 294:770 (1981).

Poiesz, B.J., et al, *Proc Natl Acad Sci* (USA), 77:7415 (1980).

Popovis, M., et al, *Science,* 219:856 (1983).

Seiki, M., et al, *Proc Natl Acad Sci* (USA) 80:3618 (1983).

3. BACKGROUND OF THE INVENTION

The human T-cell leukemia viruses (HTLV) represent a family of T-cell retroviruses with three known members. HTLV type I (HTLV-I) has transforming activity in vitro and is etiologically linked to adult T-cell leukemia, which is known to be endemic in several parts of the world. HTLV-II is another retrovirus having transforming capacity in vitro, and has been isolated from a patient with a T-cell variant of hairy cell leukemia. HTLV-III, which has also been called lymphadenopathy-associated virus and is now known as the human immunodeficiency virus (HIV). is lytic for certain kinds of T cells and has been linked to the etiology of acquired immunodeficiency syndrome (AIDS). Unlike the HTLV-I and -II viruses. HTLV-III is not known to have in vitro transforming activity.

A monoclonal antibody (Mab) reactive against HTLV-I, has been reported (Matsushita). The antibody, designated 0.5α, is an IgG$_1$ Mab which binds to the cell membrane of T-cells infected with HTLV-I, causing cell lysis in the presence of complement. Electroblot studies indicate that the Mab reacts with the major envelop protein of HTLV-I (Matsushita). This protein, designated gp46, is the outer membrane component of the env gene product. A proviral HTLV-I genome has been isolated and sequenced in its entirety (Seiki). Using a competitive inhibition binding assay, it was observed that 15 out of 15 patients with adult T-cell leukemia had antibodies that blocked the binding of the Mab to disrupted HTLV-I virions (Matsushita). The antibody does not appear to bind to either the HTLV-II or HTLV-III virions or to infected cells.

Although the above-discussed studies indicate the possibility of using an anti-HTLV-I antibody for diagnosing HTLV-I infection, this approach has two major drawbacks. First, the assay system is relatively laborious, requiring both a source of HTLV-I virions, infected cells, or fractionated gp46 protein, and anti-HTLV-I Mabs combined into a competitive binding assay format. Secondly, whole virions, or even fractionated proteins thereof, are likely to react with more than one epitope-specific anti-HTLV-I antibody, thereby decreasing both the sensitivity and specificity of the test.

4. SUMMARY OF THE INVENTION

It would therefore be useful, for diagnosing HTLV-I infection, to provide one or more HTLV-I peptide antigens which are immunoreactive with antibodies known to be present in all patients infected with HTLV-I, including those with T-cell leukemia, and which may be specifically diagnostic of certain stages of HTLV-I infection. Such antigen(s) could be used in either a simple solid phase or homogeneous antibody-binding assay for rapid determination of antibodies which are diagnostic of HTLV-I infection. It is one general object of the invention to provide an HTLV-I peptide antigen which is specific for an anti-HTLV-I antibody present in patients with HTLV-I related T-cell leukemia.

Another object of the invention is to provide a simple, rapid, relatively inexpensive immunoassay which uses such antigen.

The present invention includes a recombinant peptide antigen which is (a) derived from HTLV-I envelope protein gp46 and (b) immunoreactive with anti-HTLV-I antibody present in individuals with T-cell leukemia. The antigen is non-glycosylated and preferably includes the amino acid sequence:

Leu—Leu—Val—Asp—Ala—Pro—Gly—Tyr—Asp—Pro—Ile—
—Trp—Phe—Leu—Asn—Thr—Glu—Pro—Ser—Gln—Leu—
—Pro—Pro—Thr—Ala—Pro—Pro—Leu—Leu—Pro—His—
—Ser—Asn—Leu—Asp—His—Ile—Leu—Glu—Pro—Ser.

In another aspect of the invention, the antigen is preferably immunoreactive with an antibody present in the serum of HTLV-I-infected individuals, including individuals with T-cell leukemia.

The invention also includes a system and method for detecting HTLV-I infection in a test individual. In practicing the method, an antigen of the type described is reacted with serum from the test individual, and then examined for the presence of bound antibody. The assay system may be a solid phase type, in which the antigen is carried on a solid support, or a homogeneous system, in which the antigen is associated with a reporter, where antibody binding to the antigen modulates the reporter signal which is detected.

In still another aspect, the invention includes a vaccine for immunizing an individual against T-cell leukemia. The vaccine includes a recombinant peptide of the type described, in a pharmaceutically acceptable adjuvant.

These and other objects and features of the invention will become more fully understood when the following detailed description of invention is read in conjunction with the accompanying figure, which shows at FIG. 1A, a portion of an HTLV-I genome:

at FIG. 1B, expanded regions of the genome corresponding to those nucleotide sequences encoding three peptide antigens of the invention:

and at FIG. 1C, the gene sequence and corresponding amino acid sequence of the three peptide antigens.

DETAILED DESCRIPTION OF THE INVENTION

I. PREPARING HTLV-I PEPTIDE ANTIGENS

This section describes the preparation of HTLV-I peptide antigens which are immunoreactive with anti-HTLV-I antibodies found in individuals with HTLV-I-related T-cell leukemia. The antigens are prepared using random HTLV-I gene sequences 100–300base pairs in length cloned in a suitable expression vector, then selected with antibody for expression of immunoreactive peptide.

A. HTLV-I Genomic Libraries

Genomic libraries of HTLV-I are prepared conventionally from cellular DNA containing an HTLV-I proviral genome. Duplex DNA may be prepared from HTLV-I infected cells, including T-cells isolated from patients known to be infected with HTLV-I virus, or known cells lines, such as HUT 102-B2 (Poiesz), MT-2 (Miyoshi), and MJ-tumor (Popovic) cells, all of which have been shown to produce HTLV-I virus. The viral genome is integrated into host DNA in these cells. Methods for preparing cell lines containing the HTLV-I genome are detailed in the above references.

The total host genomic DNA from the above cell line is partially digested with a frequent cutter, such as HaeIII or AluI under conditions which produce partial digest fragments in the 15–20 kbase size range, and the digested material is fractionated, for example, by sucrose gradient centrifugation, to isolate the 15–20 kbase fragments. The fragments are then cloned into a suitable cloning vector, and preferably a phage cloning vector which can efficiently incorporate a 15–20 kbase insert. In a preferred method, the isolated fragments are treated with EcoRI methylase, and EcoRI linkers are ligated to their ends under standard conditions (Maniatis), and then cloned into a phage vector, such as λ Charon 4a, having a unique EcoRI insertion site.

The cloned genomic fragments are screened with a probe which is complementary to a selected sequence of the full-copy HTLV-I genome. HTLV-I sequences are known (Seiki), as are methods for producing radiolabeled synthetic oligonucleotide probes for selected sequences. In addition, synthetic oligonucleotides of specified sequences can be made by commercial services, such as provided by Synthetic Genetics, Inc. (San Diego CA). Using such an oligonucleotide probe, molecular clones containing HTLV-I sequences are isolated from the library by standard hybridization procedures (Maniatis, p. 322). The clones can first be analyzed by restriction site analysis, to confirm that the full viral genomic sequence is present, as indicated by the presence of direct long terminal repeats which flank the integrated viral genome. The identified molecular clone is digested with a suitable endonuclease to release the full-copy viral genome. A preferred endonuclease for this purpose is SacI, which cuts the viral genome in the long terminal repeats (LTR) at either end of the viral coding sequences, but does not produce internal cleavage. If the clonal HTLV-I genome is a variant with a third internal SacI site, an appropriate restriction enzyme will be chosen to isolate the full-length genome. The purified full-copy sequence is about a 9.5 kilobase fragment. Alternatively, a fragment of the genome representing the env gene sequences alone may be purified for production of the expression library.

Alternatively, cloning vectors containing full-copy HTLV-I duplex DNA have been reported (Seiki) and may be obtained directly from the investigators, as indicated in Example I.

To produce the desired HTLV-I genomic library, the full copy HTLV-I insert is excised from the above cloning vector, such as by complete digestion with SacI. and isolated as a 9.5 kilobase fragment as described in Example I. The isolated full-copy fragment is digested to produce DNA fragments, and preferably random fragments with sizes predominantly between about 100–300 base pairs. Example I describes the preparation of such fragments by DNAse digestion. Because it is desired to obtain peptide antigens of between about 30–100 amino acids, the digest fragments are preferably size fractionated, for example by gel electrophoresis, to select those in the approximately 100–300 base pair size range.

The genomic digest fragments are inserted into a suitable cloning vector, and preferably an expression vector which permits expression of the coded-for peptide in a suitable host. One preferred expression vector is λgt11, which contains a unique EcoRI insertion site 53 base pairs upstream of the translation termination codon of the β-galactosidase gene. Thus, the inserted sequence will be expressed as a β-galactosidase fusion protein which contains most of the N-terminal portion of the β-galactosidase gene, the heterologous peptide, and at least a portion of the C-terminal region of the β-galactosidase gene. This vector also produces a temperature-sensitive repressor (cI857) which causes viral lysogeny at permissive temperatures, e.g., 32° C. and leads to viral lysis at elevated temperatures. e.g., 42° C. Advantages of this vector include: (1) highly efficient recombinant generation, (2) ability to select lysogenized host cells on the basis of host-cell growth at permissive, but not non-permissive temperatures, and (3) high levels of recombinant fusion protein production. Further, since phage containing a heterologous insert produces an inactive β-galactosidase enzyme, phage with inserts can be readily identified by a β-galactosidase colored-substrate reaction.

For insertion into the expression vector, the viral digest fragments may be modified, if needed, to contain selected restriction-site linkers, such as EcoRI linkers, according to conventional procedures. Example I illustrates methods for cloning the digest fragments into λgt11, which includes the steps of blunt-ending the fragments, adding EcoRI linkers and ligating the fragments with EcoRI-cut λgt11. The resulting viral genome library may be checked to confirm that a relatively large (representative) library has been produced. This can be done, in the case of the λgt11 vector, by infecting a suitable bacterial host, plating the bacteria, and examining the plaques for loss of β-galactosidase activity. Using the procedures described in Example I, about 60% of the plaques showed loss of enzyme activity. The level of background phage showing loss of enzyme activity is relatively low, as seen in Example I.

B. Peptide Antigen Expression

The genomic library formed above is screened for production of peptide antigen (expressed as a fusion protein) which is immunoreactive with the human anti-HTLV-I antibody of interest. One antibody of particular interest for diagnosing HTLV-I infection is the 0.5 α antibody which, as noted above, is present in patients with T-cell leukemia related to HTLV-I infection. The antibody is produced by the EBV-transformed B-lymphocyte cell line having ATCC Deposit No. HB8755 (see Example II), and has been shown to react with the gp46 envelop protein of HTLV-I (Matsushita). This cell line is a human B-cell clone derived from a patient with HTLV-I infection and immortalized with Epstein-Barr virus. The cell line HB8755 has been re-deposited in the American Type Culture Collection, 12031 Parklawn Drive, Rockville, MD 20852, and given new ATCC Deposit No. HB 10571.

In a preferred screening method, host cells infected with phage library vectors are plated, as above, and the plate is blotted with a nitrocellulose filter, to transfer recombinant antigens produced by the cells onto the filter. The filter is then reacted with the anti-HTLV-I antibody, washed to remove unbound antibody, and reacted with reporter-labeled, anti-human antibody, which becomes bound to the filter, in sandwich fashion, through the anti-HTLV-I antibody.

Typically, phage plaques which are identified by virtue of their production of recombinant antigen of interest are re-examined at a relatively low density, for production of antibody-reactive fusion protein. The screening procedures described in Example 2 are illustrative. Several recombinant phage clones which produced immunoreactive recombinant antigen were identified in the procedure.

Figure 1A:
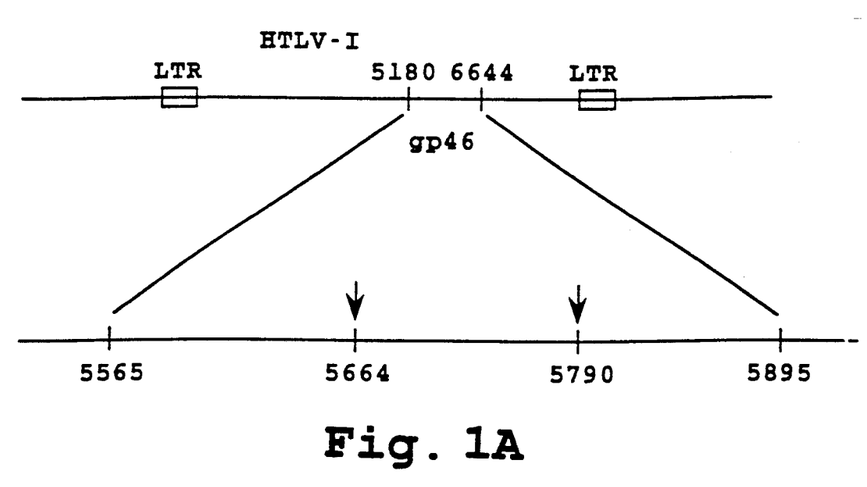
Figure 1B:
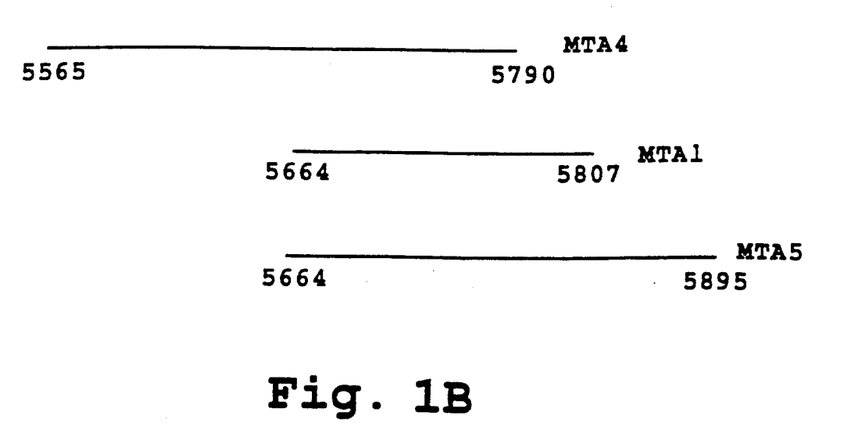
Figure 1C:
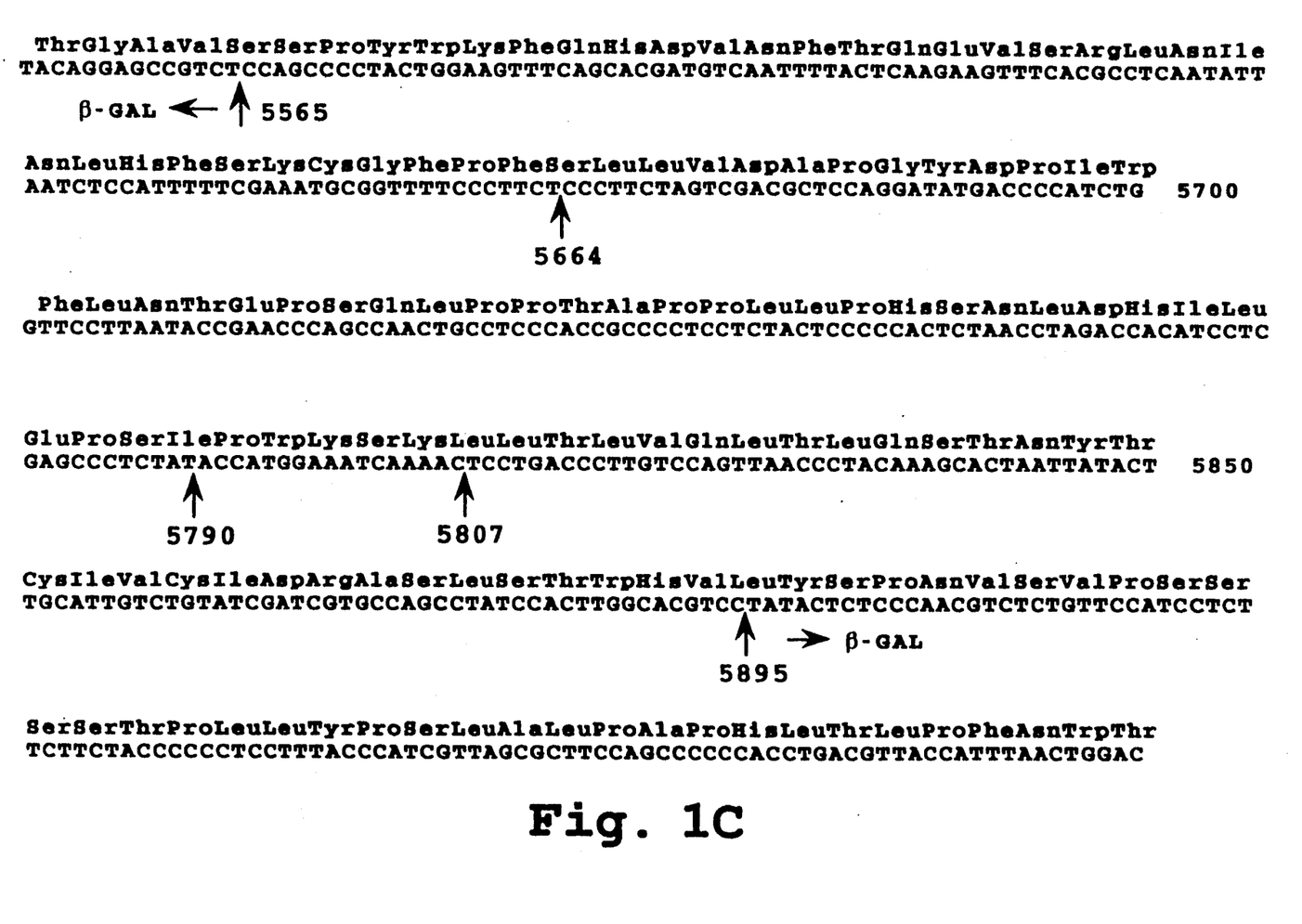

The one or more library vectors identified as above are preferably analyzed by base pair sequencing, to determine the positions of the peptide-coding regions within the HTLV-I genome. Methods for excising the heterologous insert (including adjacent coding sequences of the fusion protein, if desired) from the selected library vectors, and for purifying and sequencing the excised fragments generally follow known procedures, as outlined in Example III. The coding sequences of three peptides which were found to be immunoreactive with the 0.5 α antibody are shown in FIG. 1C. The three heterologous sequences were matched with the known sequence of HTLV-I (Seiki). As discussed more fully in Example III, all of the sequences fall within base pairs 5565 and 5895 of the HTLV-I genome, within the gene coding for the HTLV-I envelope protein gp46 as seen in FIG. 1H, and have an overlapping coding sequence (defined by the two arrows in the drawing) between base pairs 5664 and 5790 as seen in FIG. 1B. As seen in the drawing, part C, the overlapping sequence codes for a 41 amino acid peptide antigen having the following amino acid sequence:

Leu—Leu—Val—Asp—Ala—Pro—Gly—Tyr—Asp—Pro—Ile—
—Trp—Phe—Leu—Asn—Thr—Glu—Pro—Ser—Gln—Leu—
—Pro—Pro—Thr—Ala—Pro—Pro—Leu—Leu—Pro—His—Ser—
—Asn—Leu—Asp—His—Ile—Leu—Glu—Pro—Ser.

More generally, the peptides of the invention are (a) derived from the HTLV-I envelope protein gp46, and (b) immunoreactive with an anti-HTLV-I antibody present in individuals with T-cell leukemia. Here the term "derived from" means that synthesis of the recombinant peptide is directed by a coding sequence which is substantially identical in codon sequence to a major region of the HTLV-I envelope protein gp46 coding region between base pairs 5664 and 5790, as identified herein.

The selected clones are used for scale-up production, for purposes of recombinant protein purification. Scale-up production is carried out using one of a variety of reported methods for (a) lysogenizing a suitable host, such as E. coli, with a selected λgtll recombinant (b) culturing the transduced cells under conditions that yield high levels of the heterologous peptide, and (c) purifying the recombinant antigen from the lysed cells.

In one preferred method, involving the above λgtll cloning vector, a high-producter E. coli host, BNN103, is infected with the selected library phage, and replica plated on two plates. One of the plates is grown at 32° C., at which viral lysogeny can occur, and the other at 42° C., at which the infecting phage is in a lytic stage, and therefore prevents cell growth. Cells which grow at the lower, but not the higher temperature, are therefore assumed to be successfully lysogenized.

The lysogenized host cells are then grown under liquid culture conditions which favor high production of the fused protein containing the viral insert, and lysed by rapid freezing to release the desired fusion protein. These methods are detailed in Example IV and V below.

C. Peptide Purification

The recombinant peptide is purified by standard protein purification procedures which may include differential precipitation, molecular sieve chromatography, ion-exchange chromatography, isoelectric focusing, gel electrophoresis and affinity chromatography. In the case of a fused protein, such as the β-galactosidase fused protein prepared as above, the protein isolation techniques which are used can be adapted from those used in isolation of the native protein. Thus, for isolation of a β-galactosidase fusion protein, the protein can be isolated readily by simple affinity chromatography, by passing the cell lysis material over a solid support having surface-bound anti-β-galactosidase antibody. This approach is used in Example VI for purification of the MTA4/β-galactosidase fusion protein whose viral peptide sequence is shown in the drawing.

II. Utility

This section describes uses of the antigenic peptide of the invention for diagnosing HTLV-I infection, and as a potential vaccine against HTLV-I infection.

A. Diagnostic Applications

Three basic types of diagnostic applications of the peptide antigens will be described. The first is based on inhibition of complement-mediated, antibody-dependent cytolysis by the peptide. In this method, serum from a test individual is reacted with HTLV-I infected T-cell clones in the preserve of complement. The presence of anti-HTLV-I antibody is evidenced by cell lysis, as judged, for example, by trypan blue dye exclusion. Where cell lysis is observed, the specificity of the anti-HTLV-I antibody for the HTLV-I peptide is demonstrated by first reacting the serum with excess peptide, then mixing the serum with cells in the presence of complement. Antibody specificity is indicated by a substantial decrease in cell lysis. This method is described in Example VII. The method can also be used to quantitate the antibody titer in the analyte serum, by titrating the serum with increasing amounts of peptide, and determining the peptide concentration where a noticeable effect on the extent of cell lysis is first observed.

The second general assay type is a solid-phase immunoassay. In this method, a solid phase reagent having surface-bound peptide is reacted with analyte serum, under conditions which allow antibody binding to the peptide on the reagent. After washing the reagent to remove unbound serum components, the reagent is reacted with reporter-labeled anti-human antibody, to bind reporter to the reagent in proportion to the amount of bound anti-HTLV-I antibody on the solid support. The reagent is again washed, to remove unbound labeled antibody, and the amount of reporter associated with the reagent is determined. Typically, as in the system described in Example VIII, the reporter is an enzyme which is detected by incubating the solid reagent in the presence of a suitable fluorometric or colorimetric substrate.

The solid surface reagent in the above assay is prepared by known techniques for attaching protein material to solid support material, such as polymeric beads, dip sticks, or filter material. These attachment methods generally include non-specific adsorption of the protein to the support (as in the filter support described in Example VIII) or covalent attachment of the protein, typically through a free amine group, to a chemically reactive group on the solid support, such as an activated carboxyl, hydroxyl, or aldehyde group.

The third general assay type is a homogeneous assay, in which antibody binding to a solid support produces some change in the reaction medium which can be directly detected in the medium. Known general types of homogeneous assays proposed heretofore include (a) spin-labeled reporters, where antibody binding to the antigen is detected by a change in reporter mobility (broadening of the spin splitting peaks), (b) fluorescent reporters, where binding is detected by a change in fluorescence efficiency, (c) enzyme reporters, where antibody binding effects enzyme/substrate interactions, and (d) liposome-bound reporters, where binding leads to liposome lysis and release of encapsulated reporter. The adaptation of these methods to the peptide of the present invention follows conventional method for preparation of homogeneous assay reagents.

In each of the three general assays described above, the assay method involves reacting the serum from a test individual with the antigen, and examining the antigen for the presence of bound antibody. In the first assay, the examining is done by observing the decrease in antibody-mediated cytolysis, when the antibody is bound to the peptide. In the solid-phase assay, the examining involves attaching a labeled anti-human antibody to the antibody being examined, and measuring the amount of reporter bound to the solid support. And in the third assay type, the examining is done by observing the effect of antibody binding on a homogeneous assay reagent.

B. Peptide Vaccine

The peptide antigen of the invention may also be used as a vaccine, to induce cytotoxic anti-HTLV-I antibodies. Here it is important to note that the 0.5 α monoclonal antibody is cytotoxic in the presence of complement for T-cells infected with HTLV-I virus. The peptide is formulated with a suitable carrier/adjuvant and injected at periodic intervals, until a significant titer of cytotoxic anti-HTLV-I antibody is detected in the serum. The vaccine would provide protection, by antibody-mediated cytoxicity, against early HTLV-I infection.

From the foregoing it can be appreciated how various objects and features of the invention are achieved. The peptide antigen of the invention is specifically reactive with an anti-HTLV-I antibody which is diagnostic of adult T-cell leukemia, and thus can be used in a rapid and inexpensive assay for T-cell leukemia. At the same time the peptide antigen elicits a cytotoxic antibody response as defined by the pre-existing 0.5 α monoclonal antibody.

The following examples illustrate various aspects of the invention, but are in no way intended to limit the scope thereof.

Materials

The materials used in the following Examples were as follows:

Enzymes: DNAse I and alkaline phosphatase were obtained from Boehringer Mannheim Biochemicals (BMB, Indianapolis, IN): EcoRI, EcoRI methylase, DNA ligase, and Polymerase I, from New England Biolabs (NEB, Beverly, MA); and RNase was obtained from Sigma (St. Louis, MO).

Other reagents: EcoRI linkers were obtained from NEB: and nitro blue tetrazolium (NBT), 5-bromo-4-chloro-3-indolyl phosphate (BCIP), 5-bromo-4-chloro-3-indolyl-$\beta$-D-galactopyranoside (X-gal) and isopropyl $\beta$-D-thiogalactopyranoside (IPTG) were obtained from Sigma.

EXAMPLE I

PREPARATION OF AN HTLV-I GENOMIC LIBRARY

Source of Genomic Material: Bacteriophage containing a full-copy DNA insert derived from the HTLV-I genome was obtained from Drs. R.C. Gallo and F. Wong-Staal of the Laboratory of Tumor Cell Biology, National Institutes of Health (Bethesda, MD). The bacteriophage was digested to completion with SacI, releasing the viral genome insert. The digested material was electrophoresed on standard 10% agarose gel, and the 9.5 kilobase fragment obtained by electroelution was extracted with phenol/chloroform before ethanol precipitation.

DNA Digestion: The purified genomic DNA was suspended in a standard digest buffer (0.5M Tris HCl, pH 7.5; 1 mg/ml BSA; 10mM $MnCl_2$) to a concentration of about 1 mg/ml, and digested with DNAse I at room temperature for about 5 minutes. These reaction conditions were determined from a prior calibration study, in which the incubation time required to produce predominantly 100–300 basepair fragments was determined. The material was extracted with phenol/chloroform before ethanol precipitation.

Addition of EcoRI Linkers: The genomic fragments from above were blunt-ended with DNA Pol I under standard conditions (Huynh), then extracted with phenol/chloroform and precipitated with ethanol. The blunt-ended material was ligated with EcoRI linkers, under standard conditions (Maniatis, pp. 396, 397), then digested with EcoRI to remove redundant linker ends. The material was then agarose gel fractionated to remove non-ligated linkers and to size select (see below).

Size selection: The resultant fragments from the previous step were analyzed by electrophoresis (5–10V/cm) on 1.2% agarose gel, using $\phi$X174/HaeIII and $\lambda$/HindIII size markers. The 100–300 bp fraction was eluted onto NA45 strips (Schleicher and Schuell), which were then placed into 1.5 ml microtubes with eluting solution (1 M NaCl, 50 mM arginine, pH 9.0), and incubated at 67° C. for 30–60 minutes. The DNA, now in solution, was extracted with phenol/chloroform and precipitated with ethanol. The pellet was resuspended in 20 μTE (0.01 M Tris HCl, pH 7.5, 0.001 M EDTA).

Ligation into λgt11 and In Vitro Packaging

λgt11 phage vector (Huynh) was obtained from Promega Biotec (Madison, WI). This cloning vector has a unique EcoRI cloning site 53 base pairs upstream from the β-galactosidase translation termination codon. The genomic fragments from above were introduced into the EcoRI site by mixing 0.5-1.0 μg EcoRI-cleaved gt11, 0.5-3 μl of the above HTLV-I genomic fragments, 0.5 μl 10X ligation buffer (above), 0.5 μl ligase (200 units), and distilled water to 5 μl. The mixture was incubated overnight at 14° C., followed by in vitro packaging, according to standard methods (Maniatis. pp. 256-268).

The packaged phage were used to infect $E.\ coli$, strain KM392, obtained from Dr. Kevin Moore, DNAX (Palo Alto, CA). Alternatively. $E.\ coli$, strain Y1090, available from the American Type Culture Collection (ATCC #37197), could be used. The infected bacteria were plated and the resultant colonies were checked for loss of β-galactosidase activity—(clear plaques) in the presence of X-gal using a standard X-gal substrate plaque assay method (Maniatis). Table 1 below shows the number of recombinant (clear) plaques obtained with insertion of the EcoRI-ended HTLV-I fragments (row 1). An EcoRI linker control (row 2) and no background control (row 3) were also run. As seen, about 50% of the phage plaques showed loss of enzyme (recombination). The background levels either in the presence of absence of EcoRI linkers were less than 15%. About 60% of the plaques showed loss of enzyme activity. The phage material contained about $10^6$ plaque-forming units (pfu)/ml.

TABLE 1

| Insert | Vector | Clear/Total | % Rec |
|---|---|---|---|
| 1. SacI insert 3.25 μl | 1 μl | 100/200 | 50 |
| 2. EcoRI linker 3.25 μl | 1 μl | 25/178 | 14 |
| 3. Control | 1 μl | 50/400 | 13 |

EXAMPLE II

SCREENING FOR GP46 CODING INSERTS

Monoclonal Antibody. Purified 0.5 α antibody derived from a human cell line (ATCC HB8755(new ATCC No. HB10571)) was provided by Dr. Samuel Broder of the National cancer Institute, National Institutes of Health (Bethesda, MD). Mouse anti-human IgG antibody covalently derivatized with alkaline phosphatase was obtained from Promega Biotec (Madison, WI).

Identification of recombinant gp46: A lawn of KM392 cells infected with about $10^4$ pfu of the phage stock from Example I was prepared on a 150 mm plate, and incubated, inverted, for 5-8 hours at 37° C. The lawn was overlaid with a nitrocellulose sheet, causing transfer of secreted HTLV-I recombinant protein from the plaques to the paper. The plate and filter were indexed for matching corresponding plate and filter positions.

The filter was washed twice in TBST buffer (10mM Tris, pH 8.0, 150 mM NaCl, 0.05% Tween 20), blocked with AIB (TBST buffer with 1% gelatin), washed again in TBST, and incubated overnight after addition of 0.5 α monoclonal antibody (diluted to 1-2 μg/ml in AIB, 12-15 ml/plate). The sheet was washed twice in TBST, then contacted with enzyme-labeled anti-human antibody, to attach the labeled antibody at filter sites containing antigen recognized by the 0.5 α antibody. After a final washing, the filter was developed in a substrate medium containing 33 μl NBT (50 mg/ml stock solution maintained at 5° C.) mixed with 16 μl BCIP (50 mg/ml stock solution maintained at 5° C.) in 5 ml of alkaline phosphatase buffer (100 mM Tris, 9.5, 100 mM NaCl, 5 mM $MgCl_2$). Purple color appeared at points of antigen production, as recognized by the 0.5× antibody.

Secondary plating: The areas of antigen production determined in the previous step were replated at about 100-200 pfu on an 82 mm plate. The above steps, beginning with a 5-8 hour incubation, through NBT/BCIP development, were repeated in order to identify plaques which secreted an antigen capable of reacting with the 0.5 α antibody. The identified plaques were picked and eluted in phage buffer (Maniatis, p. 443). Three of the recombinant phage plaques which secreted an antibody-reactive peptide were selected for sequencing analysis, according to the procedures in Example III. The corresponding infecting phage have been designated MTA4, MTA1, and MTA5.

EXAMPLE III

PHAGE PURIFICATION AND DNA EXTRACTION

Phages MTA4, MTA1, and MTA5 were isolated from the plate cultures of the infected $E.\ coli$ Y1088 bacteria. These cells are available from the ATCC (ATCC #31195). The plate material was purified from bacterial debris by low-speed centrifugation, and the supernatant was poured into SW 27 tubes. RNase and DNAse were each added to a concentration of 1μg/ml each from stock solutions of 1 mg/mi. The sample was incubated for 30 minutes at 37° C. and an equal volume of a polyethylene glycol (PEG) solution containing 20% m.w. 8000 PEG, 5.8 g NaCl, 2.0g $MgSO_4.7H_2O$, 1M Tris Cl, pH 7.5, and 2% gelatin was added. The sample was placed in an ice bath for 1 hr to allow the phage particles to form a precipitate, which was then isolated by centrifugation at 10 k for about 20 minutes at 4° C.

The supernatant was decanted, and the pellet was resuspended in 0.6 ml PDB buffer (5.8 g NaCl, 2.0 g $MgSO_4.7H_2O$, 50 ml 1M Tris Cl, pH 7.5, and 5 ml 2% gelatin) and transferred to 1.5 ml polypropylene microtubes. 5 μl 10% SDS, 5 μl 0.5M EDTA, and 2.5 μl proteinase K (20 mg/ml) were added, and the samples were incubated at 50° C. for 15 minutes.

The detergent and enzyme-treated material was extracted with an equal volume of phenol/chloroform, and centrifuged to ensure separation of the phases. The aqueous phase was transferred to a new tube, and the extraction/centrifugation procedure was repeated with a mixture of chloroform and isoamyl alcohol. An equal volume of isopropanol was added, the sample was inverted several times to mix, and cooled to −70° C. for 20 minutes. The sample was centrifuged for 5 minutes and the supernatant was decanted. The pellet was washed in 70% ethanol, briefly dried in a 37° C. heat block, and resuspended in 100 μl TE buffer, pH 7.5.

The isolated phage DNA was digested with KpnI and SacI and then combined with KpnI/SacI cut plasmid vector pGEM-3 (Promega Biotec) to isolate a plasmid recombinant with the insert of interest. The HTLV-I insert then was sequenced using the standard dideoxy sequencing procedure and forward and reverse primers for λgtll sequences flanking the EcoRI insertion site.

The figure shows the coding sequence and corresponding amino acid sequence of a portion of the fused protein formed by the above methods, for each of the three fused peptides examined. A terminal G base of the β-gal gene and the adjacent CC bases of the env gene contributed by each of the three insert sequences yield a GCC (Ala) codon, replacing the Ser codon which normally occurs at that codon position of all three HTLV-I env inserts. As shown, the insert in the MTA4 includes a 225 base pair sequence extending from base 5565 to 5790 of the HTLV-I coding region, corresponding to amino acids 129 to 203 (74 amino acids) of the gp46 sequence. The MTA1 insert includes a 143 base pair sequence extending from bases 5664 to 5807 of the HTLV-I coding region, corresponding to amino acids 162 to 209 (47 amino acids) of the gp46 sequence. The insert of the MTA5 phage also begins at base 5664, and extends to base 5895. This 231 basepair sequence covers amino acids 162 to 239 (77 amino acids) of the gp46 protein.

The region of insert overlap, from 5664 to 5790, includes the 41 amino acid sequence from amino acids 161 to 203 of the native gp46 protein. The number of HTLV-I-derived amino acids for the three peptides is calculated by including the interrupted 5'-end Ser codon which in the modified fused-protein coding region, is translated as Ala in recombinant peptide, but not including the 3'-end interrupted codon (which is not translated in the recombinant peptide). Thus the peptides described herein (a) are less than about 80 amino acid in length and (b) and contain the immunogenic region formed by the amino acid sequence Leu-Leu-Val-Asp-Ala-Pro-Gly-Tyr-Asp-Pro-Ile-Trp-Phe-Leu-Asn-Thr-Glu-Pro-Ser-Gln-Leu-Pro-Pro-Thr-Ala-Pro-Pro-Leu-Leu-Pro-His-Ser-Asn-Leu-Asp-His-Ile-Leu-Glu-Pro-Ser which is immunoreactive with the anti-HTLV-I antibody produced by the cell line characterized by ATCC Number HB8755. (new ATCC No. HB10571)

Example IV

CONSTRUCTION OF LYSOGENS

*E. coli*, strain C600 was obtained from Dr. R. Davis, Stanford University (Stanford, CA). Alternatively, *E. coli* Y1089 (ATCC #37196) can be used. A 1 ml saturated, overnight culture of the cells was infected with one of the three phages from Example III, by adsorbing 10 μl of eluted plaque stock to 50 μl of overnight bacterial culture. The infected bacteria were spread onto LB agar plates (Maniatis, P. 440) and incubated at 32° C. The individual colonies were picked with sterile toothpicks onto corresponding grids on two separate plates. One of the plates was incubated at 32° C., and the other, at 42° C. Cells that grew at the lower temperature (indicating a lysogenic state produced by the presence of the phage repressor protein), but not at the higher temperature (because of cell lysis) were assumed to be lysogenic. Many lysogenic colonies from each of the three phage types were found.

EXAMPLE V

RECOMBINANT ANTIGEN INDUCTION FROM LYSOGENS

This example describes induction of a recombinant protein containing the HTLV-I epitope from the λgtll lysogens prepared in Example IV with the MTA4 phage. As indicated above, the antigen is produced in the form of a β-galactosidase fusion protein which also contains an N-terminal portion of the phase β-gal protein.

A superbroth was prepared containing 35 g bactotryptone, 2 g bacto-yeast extract, 5 g NaCl, and 5 ml 1N NaOH in 1 l dH$_2$O. 500 ml of the superbroth were inoculated 1:100 with a saturated overnight culture of the *E Coli* λgtll lysogens prepared in the previous example. The culture was incubated to A$_{600}$~0.4–0.5 with vigorous aeration.

In order to maximize protein production, the temperature of the culture was raised to 43°–44° C., thereby inactivating the temperature-sensitive β-galactosidase repressor gene. The temperature was maintained at 43° C. with a 65° C. water bath for 15 minutes with aeration. IPTG, which induces β-galactosidase expression by competitively binding to the β-gal repressor, was added to the broth to 1p mM to further increase protein production. The culture was returned to the 3x° C. shaker for about an hour. The cells were then pelleted at 6,00p×g for 1u minutes at 37° C., resuspended in lysis buffer (10 mM Tris, pH 7.4, 2% Triton X-100, 1% aprotinin, and 50 μg PMSF) and immediately plunged into liquid N$_2$. Lysis was completed upon thawing of the frozen samples.

EXAMPLE VI

PURIFICATION OF FUSION PROTEIN

The cell lysate obtained in the previous example was thawed and warmed to 37° C. 10 μl DNAse (1 μg/ml) was added, and the mixture incubated until the viscosity decreased. The lysate was quickly chilled on ice, clarified at 4° C. for 5 minutes in a microfuge, and loaded onto a 6 ml column of anti-β-galactosidase coupled to Sepharose 4B (Pharmacia). The column was allowed to equilibrate 1–2 hour, and washed with 7 volumes (column volumes) of TX buffer (10 mM Tris, pH 8.0, 2% Triton X-100, 50 μg/ml PMSF), followed by 2 volumes of 5mM 3,5-diiodosalicylic acid in TX buffer. Fusion protein was then eluted from the column with 35mM 3,5-diiodosalicylic acid in TX buffer. The majority of protein was eluted in the first 3–4 volumes, and removal was substantially complete after 7 volumes.

The eluted samples were desalted and concentrated using Amicon filters (Danvers, MA).

EXAMPLE VII

INHIBITION OF COMPLEMENT-MEDIATED CYTOLYSIS

HUT 102-B2 cells were obtained from Dr. R.C. Gallo, LTCB, NIH. This is a long-term cultured T-cell lines known to produce HTLV-I.

0.5α antibody (~5 μg/ml IgG) or a control isotyped matched human IgG was preincubated with MTA4 recombinant peptide or irrelevant recombinant for 30 minutes at room temperature. 50 μl of these mixtures was then added to 5×10$^5$ HUT 102B2 cells in 96-well micro titer plates, and incubated for 30 minutes at room temperature. 30 μl of rabbit complement per well was added, and incubated 1 hour at 37° C. Cell viability was determined by microscopic examination. Cell lysis was visibly inhibited by addition of the MTA4 peptide antigen, but not by preincubation with irrelevant recombinant peptide antigen. Isotyped matched human IgG, after preincubation with either recombinant antigen or irrelevant recombinant peptide antigen, had no effect on HUT 102-82 viability.

EXAMPLE VIII

SOLID-PHASE ASSAYS

Purified MTA4 peptide antigen was prepared as in Example IV, and dot blotted on nitrocellulose filters, which were then used in a solid-phase assay for determination of serum antibodies in patients with T-Cell leukemia (6 patients with HTLV-I infection). In each case, 0.1 ml of various serum dilutions, ranging from 1:000 to 1:50,000, from the test individual was added to the filter, and allowed to react at room temperature for 30 minutes. The filter was then washed two times with TBST buffer (Example II), and incubated with anti-human antibody conjugated with alkaline phosphatase, as in Example II. The presence of antibody was determined by color development in NBT and BCIP, also as in Example II.

While the invention has been described with reference to particular embodiments, methods of construction, and uses, it will be clear to those in the art that various changes and modifications can be made without departing from the invention.

It is claimed:

1. A recombinant peptide antigen which is selected from the group consisting of peptides which have less than about 80 amino acids, derived from HTLV-I envelope protein gp46, and which contain the immunogenic region formed by the amino acid sequence Leu-Leu-Val-Asp-Ala- Pro-Gly-Tyr-Asp-Pro-Ile-Trp-Phe-Leu-Asn-Thr-Glu-Pro-Ser-Gln-Leu-Pro-Pro-Thr-Ala-Pro-Pro-Leu-Leu-Pro-His-Ser-Asn-Leu-Asp-His-Ile-Leu-Glu-Pro-Ser; and (b) immunoreactive with anti-HTLV-I antibody produced by the cell line characterized by ATCC Number HB10571.

2. The recombinant peptide antigen of claim 1, which is a non-glycosylated, β-galactosidase fusion protein.

3. The recombinant peptide antigen of claim 1, which comprises the 41 amino acids of said amino acid sequence.

4. A method of detecting HTLV-I infection in a test individual, comprising reacting serum from the test individual with an antigen which is (a) selected from the group consisting of recombinant peptides which have less than about 80 amino acids, derived from HTLV-I envelope protein gp46, and which contain the immunogenic region formed by the amino acid sequence Leu-Leu-Val-Asp-Ala-Pro-Gly-Tyr-Asp-Pro-Ile-Trp-Phe-Leu-Asn-Thr-Glu-Pro-Ser-Gln-Leu-Pro-Pro-Thr-Ala-Pro-Pro-Leu-Leu-Pro-His-Ser-Asn-Leu-Asp-His-Ile-Leu-Glu-Pro-Ser; and, (b) immunoreactive with anti-HTLV-I antibody produced by the cell line characterized by ATCC Number HB10571, and examining the antigen for the presence of bound antibody.

5. The method of claim 4, wherein the antigen provided is attached to a solid support, said reacting includes contacting such serum with the support and said examining includes reacting the support and bound antibody with a reporter-labeled anti-human antibody.

6. A kit for ascertaining the presence of antibodies to HTLV-I, comprising:

a solid support with surface-bound recombinant peptide antigen, said antigens being selected from the group consisting of peptides which (a) have less than about 80 amino acid, derived from HTLV-I envelope protein gp46, and which contain the immunogenic region formed by the amino acids sequence Leu-Leu-Val-Asp-Ala-Pro-Gly-Tyr-Asp-Pro-Ile-Trp-Phe-Leu-Asn-Thr-Glu-Pro-Ser-Gln-Leu-Pro-Pro-Thr-Ala-Pro-Pro-Leu-Leu-Pro-His-Ser-Asn-Leu-Asp-His-Ile-Leu-Glu-Pro-Ser; and, (b) are immunoreactive with anti-HTLV-I antibody produced by the cell line characterized by ATCC Number HB10571, and a reporter-labeled anti-human antibody.

* * * * *